United States Patent
Schmidt et al.

(10) Patent No.: US 6,376,477 B2
(45) Date of Patent: Apr. 23, 2002

(54) COMBINATION OF AN AGENT THAT BINDS TO THE ANDROGEN RECEPTOR AND A BISPHOSPHONIC ACID IN THE PREVENTION AND/OR TREATMENT OF DISEASES INVOLVING CALCIUM OR PHOSPHATE METABOLISM

(75) Inventors: Azriel Schmidt, Bryn Mawr; Shun-Ichi Harada, North Wales; Gideon Rodan, Bryn Mawr, all of PA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/740,338

(22) Filed: Dec. 19, 2000

Related U.S. Application Data

(63) Continuation of application No. 09/038,309, filed on Mar. 11, 1998, now abandoned, which is a continuation-in-part of application No. 08/972,932, filed on Nov. 18, 1997, now abandoned.

(60) Provisional application No. 60/031,734, filed on Nov. 26, 1996, and provisional application No. 60/032,341, filed on Dec. 4, 1996.

(51) Int. Cl.⁷ .......................... A61K 31/66; A61K 31/56
(52) U.S. Cl. ........................................ 514/108; 514/170
(58) Field of Search .................................. 514/170, 108

(56) References Cited

U.S. PATENT DOCUMENTS

| | | |
|---|---|---|
| 4,621,077 A | 11/1986 | Rosini et al. |
| 5,118,667 A | 6/1992 | Adams et al. |
| 5,284,841 A | 2/1994 | Chu et al. |
| 5,462,932 A | 10/1995 | Brenner et al. |
| 5,547,685 A | 8/1996 | Cullinan |
| 5,567,695 A | 10/1996 | Labrie |
| 5,795,883 A | 8/1998 | Hesch et al. |

FOREIGN PATENT DOCUMENTS

| | | |
|---|---|---|
| EP | 0 555 845 A2 | 8/1993 |
| WO | WO 92/14474 | 9/1992 |
| WO | WO 93/24128 | 12/1993 |
| WO | WO 94/14455 | 7/1994 |
| WO | WO 95/11029 | 4/1995 |

OTHER PUBLICATIONS

Wang et al., J. of Clinical Endocrin. & Metab., vol. 81 (1996), pp. 3654–3662, "Sublingual testosterone replacement improves muscle mass and strength, decreases bon resportion, and increases bone formation . . . ".

Glueck et al., Am. J. of Hematology, vol. 48 (1995), pp. 213–220, "Idiopathic osteonecrosis, hypofibrinolysis, high plasminogen activator inhibitor, hig lipoprotein(a), and therapy with stanozolol".

Reid et al., J. of Asthma, vol. 31(1) (1994), pp. 7–18, Review article: "Glucocorticoid osteoporosis".

Chesnut III et al., Am. J. of Medicine, vol. 99 (1995), pp. 144–152, "Alendronate treatment of the postmenopausal osteoporotic woman: Effect of multiple dosages on bone mass and bone remodeling".

Davis et al., Maturitas, vol. 21, pp. 227–236 (1995), "Testosterone enhances estradiol's effects on postmenopausal bone density and sexuality".

Raisz et al., J. Clin. Endoc. Metab., vol. 81, pp. 37–43 (1996), "Comparison of the effects of estrogen alone and estrogen plus androgen on biochemical markets of bone formation and resportion in postmenopausal . . . ".

Watts et al., Obstet. Gynecol., vol. 85, pp. 529–537 (1995), "Comparison of oral estrogens and estrogens plus androgen on bone mineral density, menopausal symptoms, and lipid–lipoprotein profiles in surgical . . . ".

*Primary Examiner*—Zohreh Fay
(74) *Attorney, Agent, or Firm*—Nicole M. Wallinger; Melvin Winokur; Anthony D. Sabatelli

(57) ABSTRACT

The inhibition of natural bone formation experienced in the prophylaxis and/or treatment of bone resorption disease with a bisphosphonic acid or a pharmaceutically acceptable salt thereof is overcome by the concomitant administration of an agent that binds to the androgen receptor.

15 Claims, No Drawings

COMBINATION OF AN AGENT THAT BINDS TO THE ANDROGEN RECEPTOR AND A BISPHOSPHONIC ACID IN THE PREVENTION AND/OR TREATMENT OF DISEASES INVOLVING CALCIUM OR PHOSPHATE METABOLISM

CROSS-REFERENCE TO RELATED APPLICATIONS

This is a continuation of Ser. No. 09/038,309, filed Mar. 11, 1998, abn, which is a CIP of Ser. No. 08/972,932, filed Nov. 18, 1997 now abandoned, which in turn is a non-provisional application based on provisional applications 60/031,734, filed Nov. 26, 1996, and 60/032,341, filed Dec. 4, 1996.

SUMMARY OF THE INVENTION

This invention is concerned with a novel method for the prevention and/or treatment of diseases involving calcium or phosphate metabolism. In particular it is concerned with the prevention and/or treatment of diseases involving bone resorption, especially osteoporosis, Paget's disease, malignant hypercalcemia, periodontal disease, joint loosening and metastatic bone disease, by the administration of an agent that binds to the androgen receptor to produce a beneficial effect on bone and a bisphosphonic acid or a pharmaceutically acceptable salt thereof either combined in a single pharmaceutical formulation or as separate entities administered more or less concurrently.

This invention is also concerned with a pharmaceutical formulation in which an agent that binds to the androgen receptor and a bisphosphonic acid or pharmaceutically acceptable salt thereof are combined.

In the remainder of this specification the term "bisphosphonic acid" is meant to refer to the acid or the pharmaceutically acceptable salt thereof. Similarly, the expression, "agent that binds to the androgen receptor" refers to such agents that produce a beneficial effect on bone and includes androgen antagonists, agonists and partial agonist/antagonist agents.

BACKGROUND OF THE INVENTION

Several bisphosphonic acids are known in the art and known to be effective in the treatment of diseases involving bone resorption. Unfortunately they also inhibit overall bone formation. Attempts have been made to stimulate bone formation that has been inhibited by a bisphosphonic acid such as with injections of growth hormone, IGF-1, parathyroid hormone or transforming growth factor ($TGF_b$) which is described in U.S. Pat. No. 5,118,667. None of these attempts has been successful or widely used in patients and have been only partially successful in animals. Most importantly use of these agents involves daily injections with compounds that have multiple effects. Combination of a bisphosphonic acid and a growth hormone secretogogue also has been reported in WO95/11029.

Combinations of estrogen, which is also known to prevent bone resorption, and androgens to stimulate bone formation, have been tried (Davis et al, 1996 Maturittas 21:227–236; Raisz et al., 1996 J. Clin. Endocrinol. Metab. 81: 37–43; and Watts et al., 1995 Obstet-Gynecol. 85: 529–537). However, it is not obvious from the results of these studies that androgens would stimulate the formation of bone in the presence of a strong non-hormonal inhibitor of bone formation. As a matter of fact, it has been reported that the bisphosphonic acid, tiludronate, inhibits the anabolic effect of parathyroid hormone (Delmas, Bone, 16(6), 603–610 (1995)).

Now, with the present invention there is provided a novel method for the prevention and/or treatment of disease involving bone resorption comprising the administration of a bisphosphonic acid and an agent that binds to the androgen receptor whereby bone resorption is prevented without compromising normal bone formation induced by the androgen.

DETAILED DESCRIPTION OF THE INVENTION

The novel method of prevention and/or treatment of diseases involving bone resorption of this invention comprises the administration to a patient in need thereof of an effective amount of a bisphosphonic acid and an effective amount of an agent that binds to the androgen receptor.

The disease states involving bone resorption that can be prevented and/or treated by the novel combination of this invention are osteoporosis, Paget's disease, malignant hypercalcemia, periodontal disease, joint prostheses loosening and metastatic bone disease, especially osteoporosis.

Examples of the bisphosphonic acids that may be used as an active ingredient in the novel method and formulation of this invention include:

4-amino-1-hydroxybutylidene-1,1-bisphosphonic acid;

N-methyl-4-amino-1-hydroxybutylidene-1,1-bisphosphonic acid;

4-(N,N-dimethylamino)-1-hydroxybutylidene-1,1-bisphosphonic acid;

3-amino-1-hydroxypropylidene-1,1-bisphosphonic acid;

3-(N,N-dimethylamino)-1-hydroxypropylidene-1,1-bisphosphonic acid;

1-hydroxy-3-(N-methyl-N-pentylamino)propylidene-1,1-bisphosphonic acid;

(dichloromethyene)-bisphosphonic acid;

[1-hydroxy-3-(1-pyrrolidinyl)-propylidene] bisphosphonic acid;

(1-hydroxyyethylidene)-bisphosphonic acid;

[(cycloheptylamino) methylene] bisphosphonic acid;

(6-amino-1-hydroxyhexylidene) bisphosphonic acid;

[[(4-chloropheny) thio] methylene] bisphosphonic acid;

[1-hydroxy-2-imidazo-(1,2a) pyridin-3-ylethylidene] bisphosphonic acid;

[1-hydroxy-2-(1H-imidazole-1-yl) ethyledene] bisphosphonic acid;

1-hydroxy-2-[3-pyridyl]ethylidene-1,1-bisphosphonic acid; and 4-(hydroxymethylene-1,1-bisphosphonic acid)piperidine;

or their pharmaceutically acceptable salts.

Methods for the preparation of bisphosphonic acids may be found in, e.g., U.S. Pat. No. 3,962,432: U.S. Pat. No. 4,054,598: U.S. Pat. No. 4,267,108: U.S. Pat. No. 4,327,039: U.S. Pat. No. 4,407,761: U.S. Pat. No. 4,621,077: U.S. Pat. No. 4,624,947: U.S. Pat. No. 4,746,654: U.S. Pat. No. 4,922,077: and EPO Patent Pub. No. 0,252,504. In particular, methods for the preparation of 4-amino-1-hydroxybutylidene-1,1-bisphosphonic acid and 4-amino-1-hydroxybutylidene-1,1-bisphosphonic acid monosodium salt trihydrate may be found in U.S. Pat. No. 4,407,761 and U.S. Pat. No. 4,922,077, respectively.

The pharmaceutically acceptable salts of bisphosphonic acids may also be employed in the instant invention.

Examples of basic salts of bisphosphonic acids include ammonium salts, alkali metal salts such as potassium and sodium (including mono-, di- and tri-sodium) salts (which are preferred), alkaline earth metal salts such as calcium and magnesium salts, salts with organic bases such as dicyclohexylamine salts, N-methyl-D- glucamine, and salts with amino acids such as arginine, lysine, and so forth. The non-toxic, physiologically acceptable salts are preferred. The salts may be prepared by methods known in the art, such as in U.S. Pat. No. 4,922,077.

In the present invention it is preferred that the bisphosphonic acid is 4-amino-1-hydroxybutylidene-1,1-bisphosphonic acid. It is even more preferred that the bisphosphonic acid is a sodium salt of 4-amino-1-hydroxybutylidene-1,1-bisphosphonic acid, in particular, 4-amino-1-hydroxybutylidene-1,1-bisphosphonic acid monosodium salt trihydrate.

Examples of agents that bind to the androgen receptor that may be used as an active ingredient in the novel method and formulation of this invention include but not limited to danazol, 5a-dihydrotestosterone, testosterone, nandrolane decanoate, methyltestosterone, methanadrostenolone, stanozolol, fluoxymesterone, oxymetholone, oxandrolone, oxymethol, norethandrolone, ethylestranol, 4-androsten-19-al-3,17-dione, 19-nortestosterone, norethandrone, norethisterone, dehydroepiandrosterone, epiandrosterone sulfate, androstenedione and androstenediol, testosterone propionate, testosterone cytpionate, and testosterone enanthate, preferably testosterone.

The bisphosphonic acid and the agent that binds to the androgen receptor can be administered combined in a single dosage form, which forms another aspect of the present invention, or as separate entities administered more or less concurrently. In either method of administration, the active ingredients are provided in doses that are the same as would be administered if given as sole medicament. In the case of the bisphosphonic acid, oral doses of 2.5 to 100 mg/day are approprate. Prophylactically, doses of about 2.5 to about 10 mg/day, and especially about 5 mg/day should be employed. For the treatment of bone disease involving bone resorption daily doses of about 5 to 20 mg/day may be used, especially about 10 mg/day. In the case of the agent that binds to the androgen receptor, doses of about 0.1–100 mg/day are recommended and preferably about 0.1–10 mg/day, depending on the potency of the agent.

In the combination of the present invention the bisphosphonic acid and the agent binds to the adrogen receptor may be administered separately or in combination. In addition, the administration of one element may be prior to, concurrently with, or subsequent to the administration of the other agent.

The active ingredients of the combination of the present invention may be administered by oral, parenteral (e.g., intramuscular, intraperitoneal, intravenous or subcutaneous injection, or implant), nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active ingredient(s) is included in an amount sufficient to produce the desired effect upon the process or condition of the disease.

The pharmaceutical compositions containing the active ingredient(s) suitable for oral administration may be in the form of discrete units such as hard or soft capsules, tablets, troches or lozenges, each containing a predetermined amount of the active ingredient(s); in the form of a dispersible powder or granules; in the form of a solution or a suspension in an aqueous liquid or non-aqueous liquid; in the form of syrups or elixirs; or in the form of an oil-in-water emulsion or a water-in-oil emulsion. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Solid dosage forms for oral administration include capsules, tablets, pills, powders and granules. In such solid dosage forms, the active compounds are admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents.

Tablets containing the active ingredient in admixture with non-toxic pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin oracacia; and (4) lubricating agents such as magnesium stearate, stearic acid or talc. The tablets may be uncoated or they may be coated by known techniques to delay disintegration and absorption in the gastroinestinal tract and thereby provide a sustained action over a longer period. For example, a time delay material such as glyceryl monostearate or glyceryl disearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example calcium carbonate, calcium phosphate or kaolin. They may also be in the form of soft gelatin capsules wherein the active ingredient is mixed with water or an oil medium, for example peanut oil, liquid paraffin, or olive oil.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents.

Aqueous suspensions normally contain the active materials in admixture with excipients suitable for the manufacture of aqueous suspensions. Such excipients may be 1) suspending agents such as sodium carboxymethylcellulose, methylcellulose, hydroxypropylmethylcellulose, sodium alginate, polyvinyl-pyrrolidone, gum tragacanth and gum acacia;
2) dispersing or wetting agents which may be
   (a) a naturally-occuring phosphatide such as lecithin,
   (b) a condensation product of an alkylene oxide with a fatty acid, for example, polyoxyethylene sterate,
   (c) a condensation product of ethylene oxide with a long chain aliphatic alcohol, for example, heptadecaethyleneoxycetanol,
   (d) a condensation product of ethylene oxide with a partial ester derived from a fatty acid and a hexitol such as polyoxyethylene sorbitol monooleate, or
   (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegatable oil such as olive oil or arachis oil, or a mineral oil such as liquid paraffin or a mixture thereof. Suitable emulsifying agents may be (1) naturally-occuring gums such as gum acacia and gum tragacanth, (2) naturally-occuring phosphatides such as soy bean and lecithin, (3) esters or partial esters derived from fatty acids and hexitol anhydrides, for example, sorbitan monooleate, (4) condensation products of said partial esters with ethylene oxide, for example polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension or solution. The suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Preparations according to this invention for parenteral administration include sterile aqueous or non-aqueous solutions, suspension, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

The active ingredient(s) of this invention may also be administered in the form of suppositories for rectal administration. This composition can be prepared by mixing the drug with a suitable non-irritating excipient which is solid at ordinary temperatures but liquid at body temperature and will therefore melt in the rectum to release the drug. Such materials are cocoa butter and polyethylene gylcols.

Compositions for nasal or sublingual administration are also prepared with standard excipients well known in the art.

For topical administration the active ingredient(s) of this invention may be formulated in liquid or semi-liquid preparations such as liniments or lotions; oil-in-water or water-in-oil emulsions such as creams, ointments, jellies or pastes, including tooth-pastes; or solutions or suspensions such as drops, and the like.

The pharmaceutical composition and method of the present invention may further comprise other therapeutically active compounds usually applied in the treatment of the above mentioned pathological conditions, for instance vitamin $D_2$ and $D_3$ and hydroxylated derivatives, e.g. 1a-hydroxy-vitamin $D_3$, 1a-hydroxy-vitamin $D_2$, 1a-25-dihydroxy-vitamin $D_3$, 1a-25-dihydroxy-vitamin $D_2$, calcitonin (human, porcine or salmon), mitramycin, sodium fluoride, and non-steroid antiinflammatory drugs, such as acetylsalicyclic acid, indomethacin, naprosyn, and timegadine.

The amount of active ingredient(s) in the formulations of this invention may be varied. However, it is convenient for the unit dose, such as a tablet, to contain the amount of active ingredient(s) that would be administered in the prophylaxis or therapy of a particular bone resorption disease. Accordingly, formulations comprising 2.5 mg, 5.0 mg and 10 mg of the bisphosphonic acid and 0.125–2.5 mg, 0.25–5.0 mg and 0.5–10 mg respectively, of the androgen would be appropriate.

EXAMPLE

| Formulation Comprising Alendronate and Androgen | | |
|---|---|---|
| Ingredients | Per Tablet | Per 4,000 Tablets |
| Alendronate (monosodium salt trihydrate) | 6.55 mg | 26.2 g |
| Agent that binds to the Androgen Receptor | 0.25–5 mg | 1–20 g |
| Anhydrous Lactose, NF | 110.45 mg | 441.8 g |
| Microcrystalline Cellulose, NF | 80.0 mg | 320.0 g |

-continued

Formulation Comprising Alendronate and Androgen

| Ingredients | Per Tablet | Per 4,000 Tablets |
|---|---|---|
| Magnesium Stearate Impalpable Powder, NF | 1.00 mg | 4.0 g |
| Croscarmellose Sodium NF, Type A | 2.00 mg | 8.0 g |

The active ingredients (equivalent to 5.0 mg of bisphosphonate anhydrous free acid per tablet) are premixed with ⅓ of the microcrystalline cellulose and ½ of the anhydrous lactose in a ribbon blender for 5 minutes at 20 rpm. To the premix is added the remaining ⅔ of the microcrystalline cellulose and the remaining ½ of the anhydrous lactose and blended for 10 minutes at 20 rpm. The croscarmellose sodium is added to the blended powders and mixed for 5 minutes at 20 rpm. Finally the magnesium stearate is added to the mixture by passing it through a 90 mesh screen and blended for an additional 5 minutes at 20 rpm. The lubricated mixture is compressed to provide tablets with the equivalent of 5 mg of alendronate anhydrous free acid and 0.25–5 mg of agent that binds to the androgen receptor.

What is claimed is:

1. A method for the prevention and/or treatment of a disease involving bone resorption which comprises the administration to a patient in need thereof of an effective amount of a bisphosphonic acid or a pharmaceutically acceptable salt thereof and an effective amount of an agent that binds to the androgen receptor.

2. The method of claim 1 wherein the bone resorption disease being treated is osteoporosis, Paget's disease, malignant hypercalcemia, periodontal disease, joint prosthesis loosening or metastatic bone disease.

3. The method of claim 2 wherein the bone resorption disease being prevented and/or treated is osteoporosis.

4. The method of claim 1 wherein the bisphosphonic acid salt is alendronate.

5. The method of claim 4 wherein the agent that binds to the androgen receptor is testosterone.

6. The method of claim 2 wherein the bisphosphonic acid salt is alendronate.

7. The method of claim 6 wherein the agent that binds to the androgen receptor is testosterone.

8. The method of claim 3 wherein the bisphosphonic acid salt is alendronate.

9. The method of claim 8 wherein the agent that binds to theandrogen receptor is testosterone.

10. A pharmaceutical formulation comprising an effective amount of a bisphosphonic acid or pharmaceutically acceptable salt thereof, an effective amount of an agent that binds to the androgen receptor and a pharmaceutically acceptable carrier.

11. The formulation of claim 7 wherein the bisphosphonic acid salt is alendronate.

12. The formulation of claim 11 wherein the agent that binds to the androgen receptor is testosterone.

13. A method of overcoming the inhibition of natural bone formation during prophylaxis and/or treatment of bone resorption disease with a bisphosphonic acid or pharmaceutically acceptable salt thereof which comprises the concommitant administration of an agent that binds to the androgen receptor.

14. The method of claim 13 wherein the bisphosphonic acid salt is alendronate.

15. The method of claim 14 wherein the agent that binds to the androgen receptor is testosterone.

* * * * *